US008222488B2

(12) United States Patent
Scholthof (10) Patent No.: US 8,222,488 B2
(45) Date of Patent: Jul. 17, 2012

(54) ENHANCING EXPRESSION OF VALUE-ADDED GENES BY TRANSGENIC EXPRESSION OF TOMBUSVIRUS-BASED P19 GENE MUTANTS

(75) Inventor: Herman B. Scholthof, College Station, TX (US)

(73) Assignee: Texas A&M University System, College Station, TX (US)

(*) Notice: Subject to any disclaimer, the term of this patent is extended or adjusted under 35 U.S.C. 154(b) by 599 days.

(21) Appl. No.: 12/161,318

(22) PCT Filed: Feb. 5, 2007

(86) PCT No.: PCT/US2007/003178
§ 371 (c)(1),
(2), (4) Date: Jul. 17, 2008

(87) PCT Pub. No.: WO2007/092460
PCT Pub. Date: Aug. 16, 2007

(65) Prior Publication Data
US 2010/0269220 A1    Oct. 21, 2010

Related U.S. Application Data

(60) Provisional application No. 60/764,981, filed on Feb. 3, 2006.

(51) Int. Cl.
*A01H 1/00* (2006.01)
*C12N 15/82* (2006.01)
*C12N 15/87* (2006.01)
(52) U.S. Cl. ............ 800/288; 800/278; 536/23.71
(58) Field of Classification Search ............ None
See application file for complete search history.

(56) References Cited

FOREIGN PATENT DOCUMENTS
WO    9844097 A2    10/1998
WO    01 38512 A2    5/2001

OTHER PUBLICATIONS

Qiu et al. 2002 MPMI 15:269-280.*
Tzfira et al. (2004, TRENDS in Genetics 20:375-383.*
Baulcombe, David C. "Molecular Biology: Unwinding RNA Silencing," Science 290(5494):1108-1109, Nov. 10, 2000.
Chu, M. et al. "Genetic Dissection of Tomato Bushy Stunt Virus p19-Protein-Mediated Host-Dependent Symptom Induction and Systemic Invasion," Virology 266:79-87 (2000).
Desvoyes, Benedicte et al., "A Novel Plant Homeodomain Protein Interacts in a Functionally Relevant Manner with a Virus Movement Protein," Plant Physiol. 129:1521-1532 (Aug. 2002).
Fisher, C. L. and Pei, G. K., "Modification of a PCR-Based Site-Directed Mutagenesis Method," BioTechniques 23:570-574 (Oct. 1997).
Goldberg, K. B. et al. "A Disease Syndrome Associated with Expression of Gene VI of Caulimoviruses May Be a Nonhost Reaction," Mol,. Plant-Microbe Interact. 4(2):182-189 (1991).

Jacob, Daniela, "Recognitiion of regulatory sequences for transcription in heterologous systems" dated Jul. 15, 2003. Dissertation to obtain an academic degree at the Humboldt University in Berlin, 160 pp. (with English language translation of the Summary, 2 pages).
Shi et al., "Plasmid vector for cloning infectious cDNAs from plant RNA viruses: high infectivity of cDNA clones of tomato aspermy cucumovirus," J. General Virology, 78:1181-1183 (1997).
Mattanovich, Diethard et al., "Efficient transformation of *Agrobacterium* spp. by electroporation," Nucleic Acids Research 17(16):6747 (1989).
McNellis, Timothy et al., "Glucocorticoid-inducible expression of a bacterial avirulence gene in transgenic Arabidopsis induces hypersensitive cell death," The Plant Journal 14(2):247-257 (1998).
Omarov, Rustem et al., "Biological Relevance of a Stale Biochemical Interaction between the TombusvirusEncodeed P19 and Short Interfering RNAs," Journal of Virology, pp. 3000-3008 (Mar. 2006).
Qu, Feng and Morris, Jack, "Efficient Infection of *Nicotiana benthamiana* by Tomato bushy stunt virus is Facilitated by the Coat Protein and Maintained by p19 Through Suppression of Gene Silencing," MPMI 15(3):193-202 (2002.
Qiu, Wenping et al., "Tombusvirus P19-Mediated Suppression of Virus-Induced Gene Silencing is Controlled by Genetic and Dosage Features That Influence Pathogenicity," MPMI 15(3):269-280 (2002).
Scholthof, H. B. Tomato Bushy Stunt Virus Spread is Regulated by Two Nested Genes That Function in Cell-to-Cell Movement and Host-Dependent Systemic Invasion, Virology 213:425-438 (1995).
Scholthof, H. B. et al. "Identification of Tomato Bushy Stunt Virus Host-Specific Symptom Determinants by Expression of Individual Genes from a Potato Virus X Vector," The Plant Cell 7:1157-1172 (Aug. 1995).
Scholthof, H. B. et al, "Biological Activity of Two Tombusvirus Proteins Translated from Nested Genes is Influenced by Dosage Control via Context-Dependent Leaky Scanning," MPMI 12(8):670-679 (1999).
Scholthof, H. B. "Plant virus transport: motions of functional equivalence," Trends Plant Sci. 10:376-382 (2005).
Simmons, Christopher and Gheynst, Jean S., "Transient co-expression of post-transcriptional gene silencing suppressors and β-glucuronidase in harvested lettuce leaf tissue does not improve recombinant protein accumulation in planta," Biotechnol Lett 29:641-645 (2007). Turina, Massimo et al., "A newly identified role for Tomato bushy stunt virus P19 in short distance spread," Molecular Plant Pathology 4(1):67-72 (2003).
Vargason, J. M. et al. "Size Selective Recognition of siRNA by an RNA Silencing Suppressor," Cell 115:799-811 (2003).
Voinnet, Oliver et al., "Suppression of gene silencing: A general strategy used by diverse DNA and RNA viruses of plants," Proc. Natl. Acad. Sci. USA, 96(24):14147-14152 (Nov. 23, 1999).

(Continued)

*Primary Examiner* — Li Zheng
(74) *Attorney, Agent, or Firm* — Conley Rose, P.C.

(57) ABSTRACT

A method of enhancing expression of at least one desired gene product in a plant, comprises transgenically introducing a Tombusvirus p19/R43W mutant gene (SEQ. ID NO: 3) into the plant, expressing at least one desired gene product in the plant, wherein expression of said product is susceptible to RNA silencing; and co-expressing the transgenically introduced p19/R43W, to produce an amount of P19/R43W mutant protein (SEQ. ID NO: 4) sufficient to suppress silencing of expression of said desired gene product.

20 Claims, 5 Drawing Sheets

OTHER PUBLICATIONS

Voinnet, Oliver et al. "An enhanced transient expression system in plants based on suppression of gene silencing by the p19 protein of tomato bushy stunt virus," The Plant Journal 33:949-956 (2003).

Yamamura, Y. and Scholthof, H. B. "Pathogen Profile: Tomato bush stunt virus: A resilient model system for stying virus-plant interactions," Mol. Plant Pathol. 6(5)::491-592 (2005).

Ye, K. et al. "Recognition of small interfering RNA by a viral suppressor of RNA silencing," Nature 4:26:874-878 (2003).

Zenklusen, Daniel et al. "The Yeast hnRNP-Like Proteins Yra1p and Yra2p Participate in mRNA Export through Interaction with Mex67p," Molecular and Cellular Biology, 21:4219-4232 (Jul. 2001).

Tzfira, Tzvi et al., "Agrobacterium T-DNA integration: molecules and models," TRENDS in Genetics 20(8):375-383 (Aug. 2004).

Tzfira, Tzvi and Citovsky, Vitaly, "*Agrobacterium*-mediated genetic transformation of plants: biology and biotechnology," Science Direct (Current Opinion in Biotechnology) 17:147-154 (2006).

Office Action dated Jul. 2, 2010 issued by the Canadian Intellectual Property Office in corresponding Canadian Application No. 2,640,473 (9 pages).

International Search Report and Written Opinion dated Sep. 27, 2007 issued in corresponding international Application No. PCT/US07/03178 (7 pages).

Response to Written Opinion dated Sep. 27, 2007 and Article 34(2)(b) Amendments dated Nov. 27, 2007 (11 pages).

EPO Search Report dated Aug. 10, 2009 issued in corresponding international application No. PCT/US07/03178 (6 pages).

Examination Report dated Nov. 24, 2009 issued by the European Patent Office in corresponding Application No. 07763093.7 (1 page).

European Patent Office Application No. 07 763 093.7, Applicant: The Texas A&M University System, Office Action dated Feb. 21, 2011, 5 pages.

Hong, Seong-Hyun et al., "Expression of Recombinant GFP in *Agrobacterium*-Inoculated Leaf-Disks of *Nicotiana tabacum* Var. Xanthi," Agricultural Chemistry and Biotechnology, vol. 47, No. 3, Sep. 2004, pp. 125-128, ISSN: 1229-2737.

Simmons, Christopher W. et al., "A Model *Agrobacterium tumefaciens* Vacuum Infiltration Into Harvested Leaf Tissue and Subsequent in Planta Transgene Transient Expression," Biotechnology and Bioengineering, vol. 102, No. 3, Feb. 2009, pp. 965-970, ISSN: 0006-3592.

* cited by examiner

ENHANCING EXPRESSION OF VALUE-ADDED GENES BY TRANSGENIC EXPRESSION OF TOMBUSVIRUS-BASED P19 GENE MUTANTS

This application is the U.S. National Stage under 35 U.S.C. §371 of International Patent Application No. PCT/US2007/003178 filed Feb. 5, 2007, which claims priority of U.S. Provisional Patent Application No. 60/764,981 filed Feb. 3, 2006.

BACKGROUND OF THE INVENTION

1. Technical Field

The present invention generally relates to methods and compositions for enhancing expression of foreign genes in transgenic plants and other eukaryotes. More particularly, the invention relates to such methods and compositions employing Tombusvirus-based p19 gene mutants.

2. Description of Related Art

A frequently encountered obstacle in plant biotechnology efforts to express foreign genes in transgenic plants, is the induction of plant defense mechanisms against such foreign introductions, and thus the expression levels of the foreign genes are often sub-optimal. It is known that plants activate a process that is termed RNA silencing or RNA interference (RNAi) which specifically degrades the transgenically expressed foreign mRNA[1]. This has the direct effect of reducing or abolishing foreign protein accumulation. To counteract the effects of RNA silencing, viruses encode suppressors and the p19 protein (P19) of Tomato bushy stunt virus (TBSV) (type member of the Tombusvirus genus in the Tombusviridae) represents one of the best biochemically characterized suppressors[2]. P19 is a very potent suppressor and its transient presence greatly enhances the expression levels of foreign proteins in plants[11-13].

Figure 1:
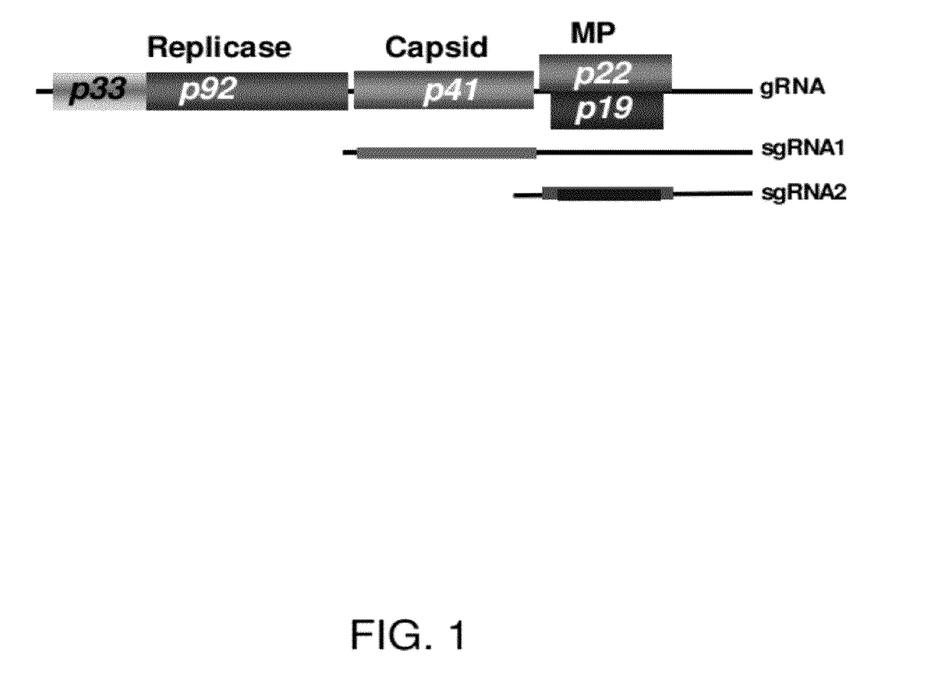
FIG. 1 is a prior art drawing showing the organization of the ~4.8-kb, single-stranded (ss) positive-sense genomic RNA (gRNA) of TBSV.

Tomato bushy stunt virus (TBSV) is an RNA plant virus that infects ca. 100 plant species in more than 20 different families. TBSV particles encapsidate a single copy of a positive-sense single-stranded RNA genome of 4775 nucleotides (nt) and its spread in plants is actively regulated by the P22 cell-to-cell movement protein and P19. The nucleotide sequence of wild-type TBSV p19 is SEQ. ID NO: 1. The amino acid sequence of wild-type TBSV P19 is SEQ. ID NO: 2. FIG. 1 shows the organization of the ~4.8-kb, single-stranded (ss) positive-sense genomic RNA (gRNA) of TBSV. The nomenclature of the five open reading frames (ORFs) (boxed regions) derives from the predicted molecular weight (in kDA) of the products. It has been shown that P19 is an intriguing multifunctional pathogenicity protein because it is a very critical host-range determinant, it is an important contributor to viral symptoms, and it has host-dependent effects on virus invasion[7-10, 14]. Recent studies suggest that these biological effects may be related to the activity of P19 as a suppressor of post-transcriptional gene silencing and virus-induced gene silencing[11,12]. It has been shown that transient co-expression of P19 prevents the onset of silencing of simultaneously introduced foreign genes, resulting in greatly (~50-fold) enhanced transient (i.e., not transgenic) expression levels of the target foreign gene[13]. While this might suggest that wild-type P19 (wtP19) could possibly be developed as a tool in plant biotechnology to substantially boost levels of target gene expression in transgenic plants, the idea is tempered by the fact that P19 expression is highly toxic to many plants[7,9]. As a consequence, hopes for establishing transgenic plants stably expressing P19 have been essentially dashed.

Several plant viruses are known to suppress gene silencing,[3] and these could also potentially serve to enhance gene expression of co-expressed value-added genes in transgenic plants. However, P19 is biochemically the best characterized and its structure has been resolved[4,5]. Genetic studies with site-specific P19 mutants targeting charged amino acids showed that a central region between amino acid positions 71 and 85 (especially amino acid 72) was essential for all the biological activities of P19 whereas other amino acids had host-dependent and activity-dependent effects[7,11]. A battery of p19 mutants were screened and a variant was identified with a single amino acid substitution at position 43 that is still active for suppression and siRNA appropriation yet is no longer toxic to plants[7,11]. More specifically, the arginine at position 43 of the p19 gene is replaced by a tryptophan, and the resulting variant or mutant p19 gene is referred to herein as p19/R43W or sometimes simply p19/43. The nucleotide sequence of p19/R43W is SEQ. ID NO: 3. The corresponding mutant protein is referred to herein as P19/R43W or P19/43, which has the amino acid sequence of SEQ. ID NO: 4. Certain biological properties of P19/R43W have also been described.[7,10,11] During infection of a plant by TBSV expressing p19/R43W, the pathogenic properties are intermediate between those of plants infected with TBSV expressing wild-type p19 and those of plants that do not express p19. As in the case of wild-type P19 expression to suppress RNA silencing of foreign gene expression[13], it was heretofore generally thought that only the relatively short term transient expression of P19/R43W in plant parts (e.g., leaves) would be possible. It was thought that the P19/R43W-expressing plant parts might provide, at best, an intermediate level of expression of a foreign gene (compared to the use of wild-type P19). Such a limited capability for enhancing transient expression (i.e., at the site of introduction in the plant part) of foreign genes would not be practical or commercially attractive for most applications. There remains a need for a practical way to improve the expression of foreign value-added genes in plants and other eukaryotic systems.

SUMMARY OF THE INVENTION

A novel mutant P19, P19/R43W, which retains its RNA silencing-suppressor activity, yet no longer has the toxicity associated with the expression of the wild-type protein in TBSV-infected plants, is employed in new compositions and methods. This previously unknown combination of desirable properties allows for the generation of p19/R43W-transgenic plants that are not hindered by the negative toxic effects of P19. It is now proposed that P19/R43W, and other similar P19 mutants that bind siRNAs and protect RNA from degradation, can be used as tools for robust and readily applicable enhancers of foreign protein expression in plants. This new technology is also believed to be potentially useful for similar purposes in other transgenic organisms. The present compositions and methods take advantage of a major feature of P19 by which its RNA silencing-suppressor function is not limited to just host plants for TBSV. In fact, the P19 suppressor function is not even limited to plants. In the studies leading to the present disclosure, in the Tombusvirus-based P19/43 mutant, the toxicity of P19 has been separated from its role as a suppressor. These combined properties of P19/43 (also referred to herein as "P19/R43W") are beneficially applied in the present methods and compositions. It was not previously known whether P19 mutants that retain the ability to suppress RNAi, but which have reduced toxicity for eukaryotic cells (referred to herein generically as "P19 m"), could (a) be introduced into eukaryotic cells as a transgene without causing toxicity to such cells; (b) if they could be successfully introduced, it was not known if the P19m sequences would be stably incorporated as transgenes; and further, (c) if they could be stably incorporated as transgenes, it was not known if they would continue to elevate the level of expression observed for other transgenes in such eukaryotic cells.

In accordance with certain embodiments of the present invention, a method of enhancing expression of at least one desired gene product (i.e., a protein or a peptide) in a plant comprises transgenically introducing a Tombusvirus p19/R43W mutant gene into the plant; expressing at least one desired gene product in the plant, wherein expression of the product is susceptible to RNAi in the plant in the absence of a RNAi suppressor; and co-expressing the transgenically introduced p19/R43W to produce an amount of P19/R43W mutant protein sufficient to suppress silencing of expression of the desired gene product, without causing lethality to the plant. In some embodiments, a desired protein or peptide is encoded by a gene that is foreign to the plant. In some embodiments, a desired protein or peptide is encoded by a gene that is native to the plant. In some embodiments, the plant is not a host plant for Tomato bushy stunt virus (TBSV). In some embodiments, the plant is *N. benthamiana*, whereas in other embodiments the plant is any of a number of vegetable species such as tomato, pepper, cucumber, spinach, beet, lettuce, and others. In still other embodiments, the plant is a crop species such as sugarbeet, potato, cereals, and others.

In certain of the above-described methods, transgenically introducing the P19/R43W into the plant comprises transformation with an *Agrobacterium* T-DNA vector comprising an expression construct containing p19/R43W (e.g., pCass4N-P19/R43W). Alternatively, another comparable T-DNA vector comprising p19/R43W may be employed.

In some of the above-described methods, expressing at least one desired gene product in the plant comprises transformation with an *Agrobacterium* T-DNA vector comprising a cDNA encoding the desired gene product. In accordance with some of the above-described methods, transgenically introducing the P19/R43W into a plant comprises inoculation of the plant with a virus vector containing an expression construct comprising P19/R43W.

Examples of "desired gene products" (also sometimes referred to as "desired proteins") for many applications include, but are not limited to, reporter proteins and peptides (e.g., GFP), and variety of gene products, including, antibodies or fragments thereof, enzymes, growth factors, cell surface receptor molecules, seed storage proteins, fungicides, and others. In still other embodiments foreign or endogenous genes are transgenically introduced which encode proteins or peptides that regulate the synthesis of certain alkaloids or other metabolites, or which are valuable as pharmaceuticals or nutraceuticals. For instance, such foreign genes may encode products that cannot be chemically synthesized or which need post-translational processing that does not occur in commonly used bacterial or yeast based bioreactor facilities.

Also provided in accordance with certain embodiments of the present invention, a transgenic plant is provided which is produced by a method comprising transgenically introducing an expressible Tombusvirus p19/R43W mutant gene into a plant; and expressing the transgenically introduced p19/R43W to produce an amount of P19/R43W mutant protein sufficient to suppress RNA silencing of expression of a desired gene product without causing lethality to the plant. In some embodiments, the method by which the transgenic plant is produced further comprises transgenically introducing at least one desired gene product into the plant, wherein expression of the desired product is susceptible to RNAi in the plant when a RNAi suppressor is absent. In some embodiments the transgenic plant co-expresses at least one desired gene product and the P19/R43W mutant protein. In some embodiments, the transgenic plant produces an amount of at least one desired gene product (per weight of plant material) that is greater than that produced by a similar plant that lacks the transgenically introduced p19/R43W.

In accordance with still another embodiment of the invention, a transgenic plant is provided which comprises p19/R43W. In some embodiments, a transgenic plant is provided which comprises a gene encoding p19/R43W integrated into the genome of the plant.

Still another embodiment of the present invention provides a seed from any one of the above-described transgenic plants. These and other embodiments, features and potential advantages will be apparent in the following detailed description and drawings and the appended claims.

DETAILED DESCRIPTION OF THE INVENTION

Figure 2:
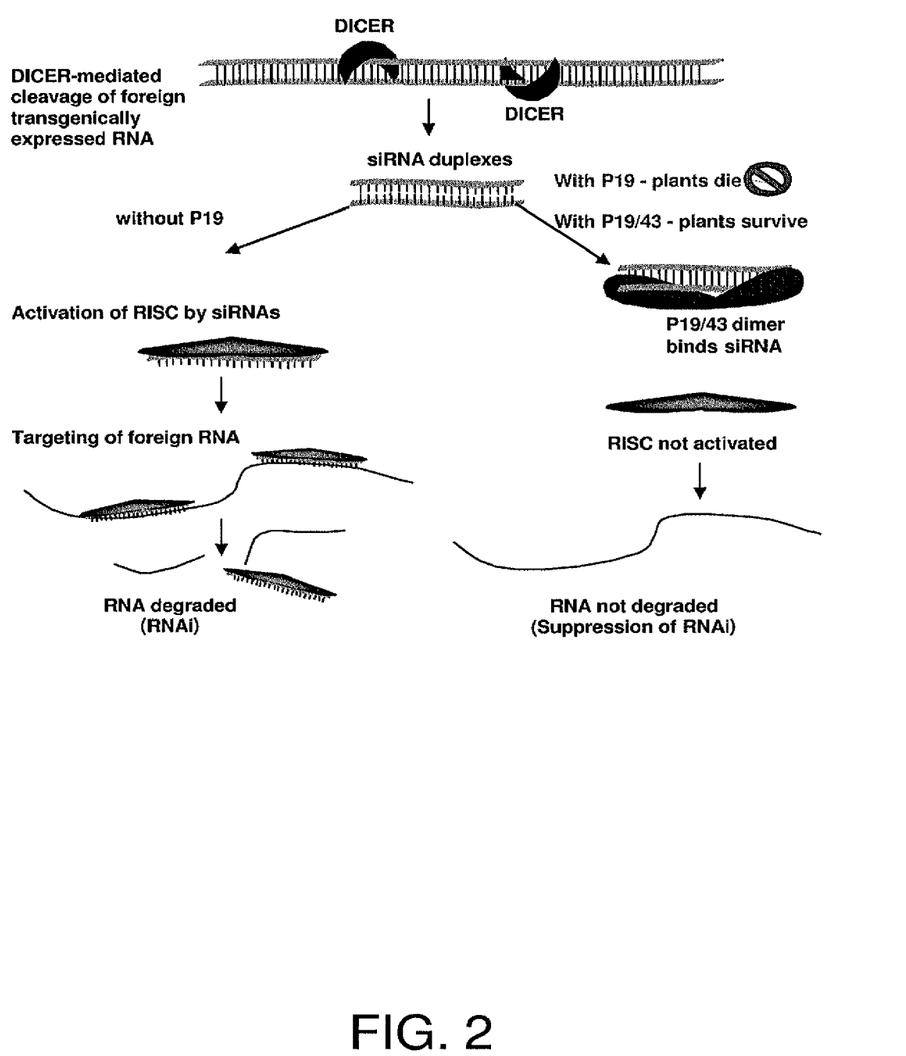
FIG. 2 is a conceptual drawing illustrating the use of P19/43-expression in transgenic plants (and other eukaryotic organisms) compared to the effect of expression of wildtype P19 and to the expression of neither.

Post-transcriptional gene silencing or RNA interference (RNAi) in plants, and the suppression of this process by specific virus proteins, are fairly recently discovered gene expression control mechanisms[1]. While the mechanism by which other suppressors function is not known, it has been recently established that a major role of P19 is to appropriate RNAi-mediated siRNAs and thus block the RNAi pathway[19]. The P19/R43W mutant has several potentially advantageous characteristics, including the following: (1) it is a stable soluble mutant P19 protein that can be produced to high amounts in plants and bacteria for subsequent protein isolation; (2) it binds siRNAs in a sequence-independent manner but the electrostatic interaction with siRNAs is different from that observed for wild-type P19; (3) like wild-type P19, P19/R43W is anticipated to bind siRNAs in vitro and in various eukaryotic systems, yet with different electrostatic properties; (4) despite its unique biochemical properties, P19/R43W still suppresses RNAi in plants and is anticipated to perform this role in various eukaryotic systems; and (5) in contrast to wild-type P19, P19/R43W no longer causes severe necrosis in the host plant. FIG. 2 illustrates the use of P19/43-expression in transgenic plants, or other eukaryotic organism, in comparison with wildtype P19. In contrast to wildtype P19, the P19/43 mutant does not cause lethal symptoms, but binds siRNAs to avoid programming of the RNA-induced silencing complex (RISC). This prevents degradation of co-expressed foreign RNA. Thus, P19/R43W will potentially substantially increase the levels of value-added (e.g., foreign) proteins produced in transgenic plants and other eukaryotic organisms.

Wild-type TBSV and p19-mutants initially show a similar infection course in *Nicotiana benthamiana*. However, in the absence of an active P19, viral RNA becomes degraded and the plants eventually recover from infection. P19 homodimers sequester 21 nucleotide (nt) virus-derived duplex short interfering RNAs (siRNAs), and it is thought that this prevents the programming of an antiviral RNA-induced silencing complex (RISC) to avoid viral RNA degradation. From an analysis of fractionated extracts from healthy or infected *N. benthamiana* plants, including assaying for in vitro ribonuclease activity and for the presence of TBSV-derived siRNAs, it was concluded that infection in the absence of a fully active RNAi suppressor induces ssRNA-specific ribonuclease activity including that conferred by a RISC-like complex, which can explain the observed recovery from infection.[19]

Two separate aspects of the P19/R43W mutant (which have been described[10,11,13,19]) take advantage of suppression of RNAi. The first aspect utilizes the positive property that suppression of gene silencing increases gene expression of introduced foreign genes. The second aspect involves reduction or elimination of the negative effect associated with suppression, since RNAi suppression often has harmful effects in causing deforming symptoms. Thus, a suppressor like the P19/43 mutant is used in plant biotechnology to optimize and maintain high levels of expression of beneficial proteins, while avoiding many or all of the normally associated harmful effects.

Now a potential solution to the seemingly insurmountable problem of enhancing foreign protein expression is provided. Even though TBSV infected p19/R43W-expressing hosts are clearly symptomatic (e.g., the plants are stunted and the leaves curl), it has been shown that the P19/R43W mutant does not cause lethal necrosis in *N. benthamiana*, and also reduces the severity of symptoms in other plants, for instance, spinach. The P19/R43W mutant forms dimers that bind to TBSV-specific siRNAs, and it retains activity for RNAi suppression (FIG. 2). This non-toxic yet suppressor-active mutant can potentially be used as a tool to block RNAi because it does not kill plants and retains the ability to suppress RNA silencing.

It is unexpected that p19/R43W is uniquely suited to generation of transgenic plants without being hindered by the toxic effects associated with wild-type P19, to create a robust and readily applicable protein expression system. Surprisingly, the transgenic p19/R43W-expressing plants typically do not develop lethal necrosis, and usually grow well enough to serve as a "biofactory" to produce commercially useful quantities of a desired foreign protein.

Using Tombusvirus Mutant P19/R43W to Enhance Expression of Foreign Proteins

To prepare a transgenic foreign protein expression system, the representative p19/R43W mutant gene is cloned into *Agrobacterium* T-DNA vectors using methods and techniques that are well known in the art. For instance, methodologies for the transformation and regeneration of plants expressing a virus (symptom causing) protein have been described by Goldberg et al.[6], the disclosure of which is hereby incorporated herein by reference. As one example, *N. benthamiana* plants are initially employed to confirm and demonstrate that the p19 mutant is biologically active for suppression. Other plants, such as *N. tabacum* and tomato are expected to further establish the general usefulness of this tool. Routine transformation and selection protocols for *N. benthamiana* are employed to identify P19 expressing lines. For this purpose, P19-specific antibodies are used, and, as controls, *N. benthamiana* transformed with a p19 gene that does not express the P19 protein[8,10] is used. RT-PCR is used to select those control lines transcribing but not translating p19. P19 mutant expression may affect the development of transgenic plants to some extent. Alternatively, if this is found to be an obstacle in a given expression system or context, an inducible promoter system[16] is used. In this way, the inducible promoter is activated for P19 expression once plants have developed fully and are no longer susceptible to negative developmental effects from constitutive expression of the P19m throughout the sensitive developmental phase.

After selecting the proper *N. benthamiana* p19-transgenic and control lines, they are examined for the effect of P19 on expression of other introduced foreign genes using three independent tests. In the initial transient expression study, the p19-transgenic plants are agroinfiltrated with *Agrobacterium* expressing a reporter gene. Expression of such genes is quantified and the expression is compared for control and P19m-transgenic plants. The level of reporter gene is expected to be routinely enhanced in the P19m transgenic plants compared to controls that do not express P19m. In FIG. 6 and Table 1, photographs C, D and I show that the agroinfiltrated leaves expressing P19/R43W (C and D) expressed elevated levels of GFP compared to the buffer-infiltrated control (I). The level of P19-expression and concomitant enhancement of GTP expression (visualized as grey areas in the center compared to dark surrounding areas) depend on the *Agrobacterium* strain (C58 or EHA) used in the test (compare C and D, and Table 1). For comparison, the effect of wtP19 is shown in A and B.

A second approach involves inoculation of plants with TBSV, Potato virus X (PVX), or Tobacco mosaic virus (TMV) vector constructs expressing reporter genes, and again the expression is compared for control and transgenic lines. Silencing often affects virus RNA accumulation. Virus-vector mediated expression of foreign genes is also expected to benefit from the presence of P19.

In a third approach, transgenic plants are co-transformed with p19m and a reporter gene. The presence of P19m is expected to substantially boost the level of expression of a second foreign gene (e.g., reporter gene expression).

According to the first approach mentioned above, generation of p19m-transgenic plants includes carrying out the following phases. These phases, or steps, are sometimes described with particular reference to the P19/R43W mutant, which is believed to be representative of other P19 mutants (sometimes collectively referred to herein as "P19 m"). These steps are potentially applicable to production of other p19m-transgenic plants expressing other P19m proteins that have at least some RNAi suppressing activity.

Generating *Agrobacterium* T-DNA Vectors that Contains the p19m-Gene.

The p19m gene is amplified by PCR from an original TBSV cDNA construct, as described by Chu et al.[7], and the resulting fragment is inserted into the appropriate *Agrobacterium* T-DNA vector, using well known methods. Several vectors may be tested, and the ones that give the highest levels of expression are selected for use. For this purpose, constructs are tested in transient agroinfiltration experiments to confirm the expression of P19m, using readily available antibodies, as previously described[11].

Evaluating the Effect of P19m on Foreign Protein Expression

The *Agrobacterium* clones expressing P19m are co-infiltrated with *Agrobacterium* expressing the green fluorescent protein (GFP). The effect of P19m-co-expression on GFP accumulation are measured and compared to that obtained for wild-type P19.

Transformation of *N. benthamiana*

The best T-DNA clones are selected for transformation of *N. benthamiana*. Transgenic plants expressing readily detectable levels of P19m, but not showing detrimental phenotypes are selected.

Testing Expression Levels

Several transgenic *N. benthamiana* lines that express P19m are agroinfiltrated with a number of T-DNA constructs expressing foreign genes, and expression levels are compared to those obtained in non-transgenic plants.

Elevating Levels of Target Gene Expression in Transgenic Plants.

The p19m-transgenic lines that perform the best during agroinfiltration assays are used for transformation with a foreign gene for which high levels of expression are desired. Parallel transformations are preferably carried out with non-transgenic plants. Expression levels in the transgenic and non-transgenic plants are then compared. Transgenic plants that yield significantly higher levels of foreign gene expression compared to the controls may be used not only for transgenic expression of value-added (i.e., foreign) genes but they may also serve as hosts for virus vectors that express the foreign genes. Similarly, other eukaryotic transgenic systems expressing the p19m mutants are also expected to be used to elevate levels of co-expressed foreign genes (either expressed transgenically or from virus vectors), for biotechnology purposes.

Although the agroinfiltration technique is described in the following examples, it should be appreciated that, alternatively, cells may be transformed by biolistic methods. For example, a direct DNA transfer technique, such as particle bombardment of intact plant cells may be employed, as described in U.S. Pat. No. 6,846,970, the disclosure of which is hereby incorporated herein by reference.

EXAMPLE

DpnI Mediated Site-Directed Mutagenesis PCR

A highly effective method for making site directed mutation on plasmids without subcloning, based on the work of Fisher and Pei[20], is employed for producing p19 mutants. The procedure includes:

(1.) Amplification of mutant DNA
(a) Combine

| DNA template | 250 ng |
| 10x Pfu DNA polymerase buffer | 5 µl |
| 10 Mm dNTP | 1 µl |
| Mutagenesis Primer-F | 125 ng |
| Mutagenesis Primer-R | 125 ng |

(b) Add ddH$_2$O to 50 µl
(c) Add 1 µl PfuTurbo DNA polymerase (STRATAGENE Cat. No. 600250, 2.5 units)

| PCR conditions | |
| --- | --- |
| 95° C. | 2 min |
| 18 cycles of: | |
| 95° C. | 1 min |
| 55° C. | 1.5 min |
| 68° C. | min/kb to length of construct |

(2.) Degradation of methylated (parental) DNA with DpnI
(a) Cool down PCR product
(b) Add 1 µl DpnI to PCR product, incubate at 37° C. overnight (3) Transformation into *E. coli*
(a) Place 100 µl high efficiency (>1×10$^8$) competent cells XL-1-Blue on ice
(b) Add 1-5 µl of digested PCR product
(c) Incubate 30 min on ice
(d) 42° C. heat shock 45-90 sec, then immediately incubate on ice for 1 min
(e) Add 1 ml LB broth to incubate 1 hr in 37° C.
(f) Plate 100 µl aliquot of culture on appropriate antibiotic medium plate
(g) Incubate overnight,
(h) Pick three colonies and incubate in LB broth overnight.

(4.) Extract plasmid DNA from the selective clones and then screen the mutant with restriction enzyme digestion (5.) Sequence the plasmid DNA from the selective clones and confirm the change Transformation of *Agrobacterium* by Electroporation Transformation of *Agrobacterium* is performed according to the method of Mattanovich et al.[21] The procedure includes:

(1.) Thaw the cells on ice. Transfer 20 µl of cells to a fresh Eppendorf tube.

(2.) Add 500-100 ng DNA and gently mix with the pipette.

(3.) Transfer 20 µl of this suspension to a chilled GIBCO-BRL electroporation cuvette (Cat. No. 11608-031) and perform electroporation using GIBCO-BRL Cell-Porator system (LCT) with following settings: Capacitance: 330 µF; DC volts: Low Ω; Charge rate: Fast; and Voltage Booster: 4Ω.

Set the cuvette in the electroporation chamber filled with ice and water. Make sure that the pointer is facing the cuvette and the plug is connected to the chamber. Charge up to 400. Turn the knob to ARM mode and press TRIGGER button for 2 sec.

(4.) Transfer the cells to 1 ml of YEP/LB medium and incubate on a shaker (100 rpm) at 28° C. for three hours.

(5.) Spread 100 µl of the culture onto YEP/LB plate (with appropriate antibiotics) and incubate for three days.

Preparation of *Agrobacterium* Stock.

An *Agrobacterium* stock is prepared as follows:
(1.) Streak *Agrobacterium* on a plate with Rifampicin.
(2.) Pick a colony and grow overnight at 28° C. in 3 ml of YM/LB (+Rif.).
(3.) Inoculate 300 ml YM/LB medium (+Rif.) with the overnight culture.
(4.) Shake at 28° C. until O.D.$_{600}$ of 0.5 is achieved.
(5.) Chill bacteria on ice for 15 mM, harvest by centrifugation at 5000 rpm at 4° C. for 10 min.
(6.) Wash 3 times in 10 ml of 10 Mm HEPES (pH 7.0)
(7.) Wash once with 10 ml of 10% glycerol
(8.) Suspend in 3 ml of 10% glycerol and aliquote 40 µl in eppendorf tubes. Cell density should be 2.5~5×10$^{10}$/ml
(9.) Freeze in liquid N$_2$ and store at −70° C.

Infiltration of *Agrobacterium* Culture into *N. Benthamiana* (Agro-Infiltration)

An *Agrobacterium* culture is infiltrated into a host plant as follows:
(1.) Incubate single colony into 2 ml LB (with appropriate antibiotics, e.g., 50 mg/ml Kan).
(2.) Grow at 28-30° C. overnight/24 hr.
(3.) Take out 250-500 µl culture (depend on its density) and add to 2 ml LB (+Kan$^{50}$).
(4.) Grow over the day, and in the evening add
1 ml Agro culture to 100 ml LB (+Kan$^{50}$)
2 ml MES (pH 5.85)
13 µl Acetosyringone (150 mM stock dissolved in DMSO)

(5.) Grow overnight (e.g., from noon to the next day), centrifuge at 6000 rpm for 15 mM at 20° C.

(6.) Suspend the cell pellet of culture in 1/10 volume of infiltration buffer (10 mM MES, pH 5.85+10 mM $MgCl_2$) and add 150 µl Acetosyringone/10 ml infiltration buffer.

(7.) Shake gently for 20-25 mM at RT, and leave it on the bench top for 3-5 hr or overnight.

(8.) Infiltrate leaves of N. benthamiana with Agro culture (without needle).

(9.) Analyze the leaf samples by western and northern analysis.

Bring the culture of Agrobacterium to an optical density ($OD_{600}$) of 1.0 to avoid toxicity.

Suppression of RNAi for Foreign Genes without Deleterious Symptoms

Figure 3:
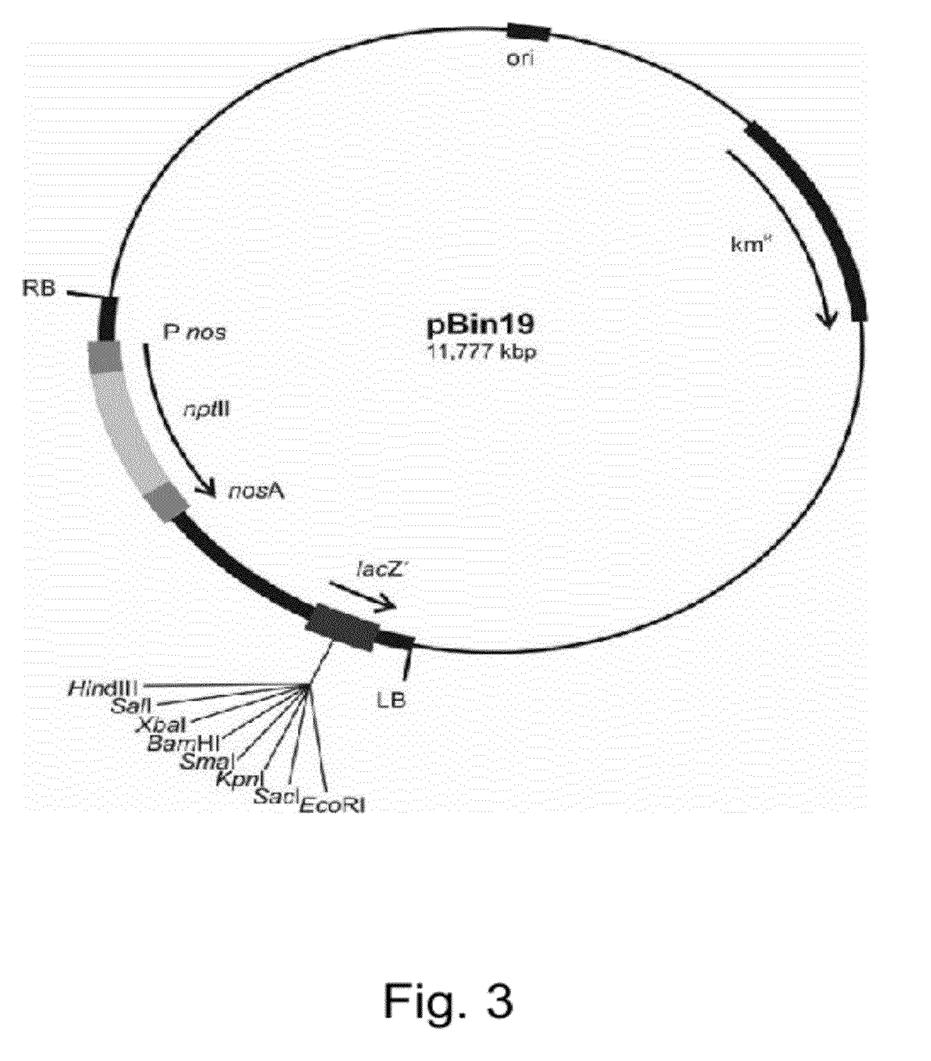
FIG. 3 is a prior art drawing illustrating the P19 expression construct pCass4N-P19.
Figure 4:
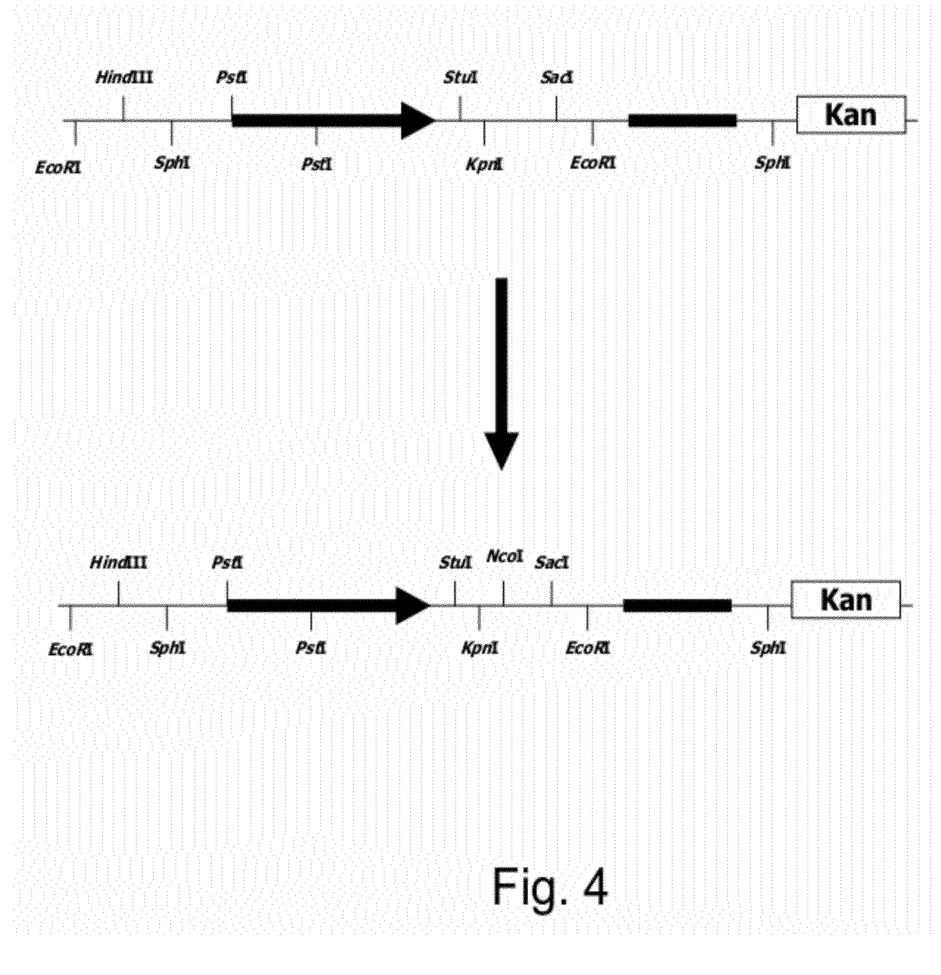
FIG. 4 is a prior art drawing illustrating the pCass4N construct used in the expression construct of FIG. 3.

Several in vivo expression constructs were tested to determine whether P19/R43W suppresses RNAi for foreign genes without deleterious symptoms. The constructs are pCB301-P19, pJL3:P19, and pCass-based constructs with p19 between NcoI and SacI of pCass4N (shown in FIG. 3)[22]. PCass4N is based on pBin19 based pCass4 ~11 Kb. TBSV p19 has been closed between NcoI and SacI of pCass-4N (shown in FIG. 4.)[23] The P19/R43W mutants were generated on the pCass4N-P19 construct using DpnI-mediated site-directed mutagenesis which includes steps on amplification of mutant DNAs with PfuI polymerase, degradation of parental (methylated) plasmid DNA with DpnI, transformation into E. coli, extraction and digestion of plasmids, and DNA sequencing. The pCass4N-P19/R43W was transformed into Agrobacterium C58 and EHA strains by electroporation and western detection is able to detect P19 from in vivo expression (within N. benthamiana). In these studies, the level of P19/R43W expression was clearly detectable but lower than the expression level of wild-type P19.

Figure 5:
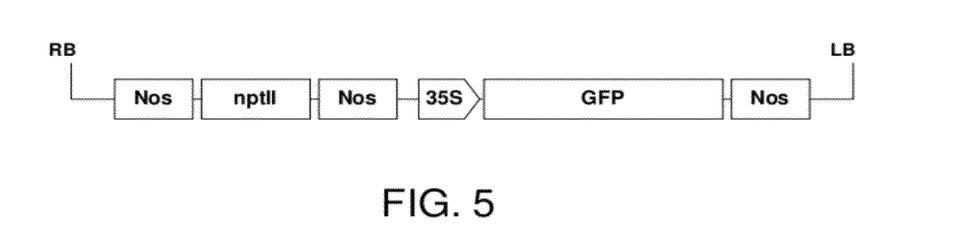
FIG. 5 shows the organization of T-DNA construct used for transient expression of GFP.
Figure 6:
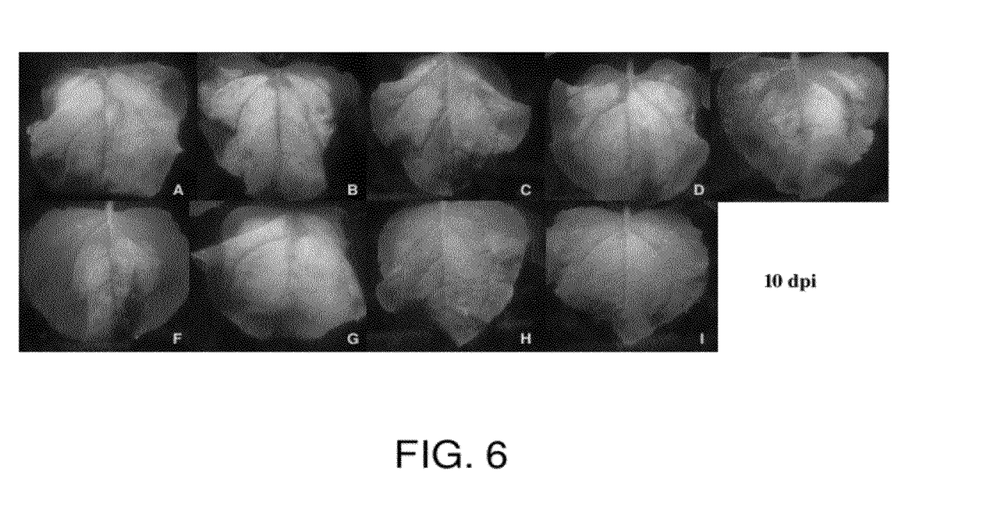
FIG. 6 is a series of photographs of *Agrobacterium* co-infiltrated leaves comparing GFP expression levels of several constructs 10 days after agroinfiltration.

Co-infiltration of P19 expression constructs with Agrobacterium expressing GFP was performed to examine the effects of P19 and P19/R43W on foreign gene expression. FIG. 5 shows the organization of T-DNA construct used for transient expression of GFP. In the figure, "35" indicates the CaMN 35S promoter and "Nos" indicates nopaline synthase terminator. Agrobacterium tumefaciens strain C58C1 was used to carry the 35S:GFP construct and infiltrated into the abaxial air spaces of 3-4-week old N. benthamiana plants. GFP signal is monitored with a 100 W handheld long-wave ultraviolet lamp from UV products (Black Ray model B100AP). FIG. 6 is a series of photographs of Agrobacterium co-infiltrated leaves comparing GFP expression levels of several constructs which are indicated in Table 1.

TABLE 1

| Photograph | P19 Construct |
|---|---|
| A | P19-C58 + GFP |
| B | P19-EHA + GFP |
| C | 43-C58 + GFP |
| D | 43-EHA + GFP |
| E | pCB301-P19| + GFP |
| F | pJL3-P19 + GFP |
| G | pKYLX7-P22 + GFP |
| H | GFP Agro only |
| I | Mock (Infiltration buffer) |

The photographs were taken 10 days after Agrobacterium co-infiltration. Transient co-expression of the GFP and P19 constructs were at the same level of $OD_{600}$, respectively. The results reconfirmed that active suppressors are able to alleviate RNAi effects and result in elevation of GFP expression. The level of RNAi suppression with the P19/R43W system was comparable to that of the P19 system, despite the fact that overall expression of P19/R43W was lower in these studies.

These agroinfiltration-mediated studies show that the P19/R43W mutant is able to enhance transient foreign gene expression in individual leaves together with a construct expressing the foreign gene of choice. Similar experiments were conducted with wild-type p19 transient experiments. The amount of p19m that was detected is lower than for wild-type p19, but sufficient to substantially elevate and maintain foreign gene expression. These studies establish the feasibility of similarly enhancing foreign gene expression in transgenic plants without killing the plant.

The non-toxic suppression-active P19 mutant, P19/R43W, meets the long felt need for a way to maintain or enhance expression of desired genes, especially foreign genes. These methods and transgenic plants and seeds have the potential for widespread appeal to the biotechnology industry and utility as virus suppressors for plant biotechnology and in other eukaryotic systems. This offers great potential for obtaining very high levels of foreign protein expression (e.g., pharmaceuticals) in plants. Such plants, as "bio-factories", are no longer subject to the plants own defenses, permitting expression of a higher level of the desired foreign protein. Such desired foreign proteins are often referred to as "value added" proteins, which add value to an agricultural crop.

Many embodiments and variations of the above-described methods, compositions, plants and seeds are encompassed by the present invention. For instance, in certain embodiments of the present invention, a method is provided for transgenically expressing TBSV-p19 gene mutants for enhancing foreign value-added gene expression in eukaryotic organisms. In certain embodiments, P19/43 is used to enhance or boost expression levels of foreign genes in transgenic plants. In certain embodiments, specific P19 amino acid substitution mutants, e.g., P19/43, are used that are no longer toxic, or are much less toxic than P19, and yet maintain the ability to suppress RNAi. In some embodiments, the mutant possesses the property to appropriate siRNAs and thus protect mRNA from RNAi-mediated degradation. These mutants are expected to be useful for enhancing gene expression in various eukaryotic systems.

Certain methods of the present invention provide transgenic plants that express suppression-active but non-toxic or reduced toxicity P19 mutants, and certain other embodiments use these plants for high levels of expression of value-added products by preventing RNAi-mediated degradation of their mRNA.

In some methods that are in accordance with the invention, an elevated level of expression of at least one desired protein is obtained in a eukaryotic cell, or an organism containing a plurality of such cells is provided. This method comprises expressing in the cell(s) a Tombusvirus P19 mutant containing the native P19 siRNA binding sites, wherein the P19 mutant suppresses silencing of expression of the desired protein, to provide a cell, or plurality of cells, producing the desired protein to a greater extent than a similar cell, or plurality of cells, not expressing the Tombusvirus P19 mutant. In certain embodiments, the cell is a plant cell, vertebrate cell, or a non-vertebrate cell. In some embodiments, the cell is a plant cell, and the organism is a plant, or a portion thereof, comprising the plant cell or plurality of plant cells. In certain preferred embodiments, the mutant is Tombusvirus P19/43. In certain embodiments, the step of expressing Tombusvirus P19/43 comprises infecting the plant, or a portion thereof, with a virus vector containing nucleotide sequences coding for P19/43 and expressing the P19/43 nucleotide sequence from the virus vector in the plant, or portion thereof, to produce P19/43. In some embodiments, the step of infecting the plant, or a portion thereof, includes introducing a virus vector operably encoding the P19/43, to provide a non-lethally infected plant capable of producing the desired protein to a greater extent than an identical non-infected plant.

In certain embodiments, production of the desired protein comprises transiently expressing the desired protein. In certain other embodiments, the method includes introducing into the plant, or a portion thereof, a virus vector containing at least one nucleotide sequence coding for at least one respective foreign gene. Expression of Tombusvirus P19/43 includes transgenically expressing P19/43 in the plant or portion thereof. In certain embodiments, transgenic expression of the desired protein is sustained.

In still another method, the desired protein is an endogenous gene product that is native to the plant. In some embodiments, the desired protein is a transgenically expressed product of a foreign nucleotide sequence in a transgenically modified plant, or portion thereof. In some embodiments, the plant is not a host plant for Tomato bushy stunt virus (TBSV).

A eukaryotic cell exhibiting an elevated level of expression of a desired protein is also encompassed by certain embodiments of the invention. This eukaryotic cell comprises a transgenically expressed RNAi suppressor comprising a mutated form of Tombusvirus P19 (P19m), wherein the P19m suppresses silencing of expression of the desired protein, such that the eukaryotic cell produces the desired protein to a greater extent than a similar cell not expressing the P19m. In some embodiments, the P19m is P19/43. In some embodiments, the eukaryotic cell is a plant cell, a non-vertebrate cell or a vertebrate cell. In some embodiments, the plant cell is comprised within a plant.

In accordance with still another aspect of the present invention, a seed is provided that is derived from a plant comprising a plurality of cells that transgenically express a RNAi suppressor comprising a mutated form of Tombusvirus P19 (P19m), wherein the P19m suppresses silencing of expression of a desired protein, such that the cell produces a desired protein to a greater extent than a similar cell not expressing the P19m.

While the preferred embodiments of the invention have been shown and described, modifications thereof can be made by one skilled in the art without departing from the spirit and teachings of the invention. The embodiments described herein are exemplary only, and are not intended to be limiting. For example, transgenic plants expressing other mutants can be generated and tested to determine if expression of other foreign target genes are substantially elevated, as described hereinabove with respect to P19/43. Accordingly, many variations and modifications of the invention disclosed herein are possible and are within the scope of the invention. For example, different promoters and terminators may be employed to drive the expression of the P19m transgene, or other transgenes sought to be expressed in the P19m transgenic plants. Various crosses between P19m transgenic plants and other transgenic plants are clearly envisioned as being within the scope of the present invention, including methods for carrying out such crosses and the plants derived from such crosses. Methods of regenerating transgenic plants from transgenic cells are also well known in the art and, therefore, based on the instant disclosure, it is considered to come within the scope of this invention to regenerate a transgenic plant from a transgenic plant cell wherein the transgenic plant cell comprises sequences encoding a P19m, as represented by P19/R43W. Seeds from such plants are also considered to be within the scope of this invention. Further, various vectors and means are known in the art for introducing transgenes into different eukaryotic cells. These methods may be used for introduction of P19m encoding sequences and other transgenes into any particular expression system under development based on the disclosure provided herein. Thus, where expression of a particular protein in a human cell is required, and where silencing of expression of the gene is found to be a problem, introduction into the cell of an appropriate P19m is also considered to be within the scope of this invention. The disclosures of all patents, patent applications and publications cited herein are hereby incorporated herein by reference to the extent that they describe materials, methods or other details supplementary to those set forth herein.

REFERENCES

1. Baulcombe, D. C. (2000) *Science* 290, 1108-1109.
2. Yamamura, Y., and H. B. Scholthof. 2005. Pathogen profile: Tomato bushy stunt virus: A resilient model system for studying virus-plant interactions. *Mol. Plant. Pathol.* 6:491-502.
3. Scholthof, H. B. 2005. Plant virus transport: motions of functional equivalence. *Trends Plant Sci.* 10:376-382.
4. Vargason, J. M., G. Szittya, J. Burgyan, and T. M. Tanaka-Hall. 2003. Size selective recognition of siRNA by an RNA silencing suppressor. *Cell* 115:799-811.
5. Ye, K., L. Malinina, and D. Patel. 2003. Recognition of small interfering RNA by a viral suppressor of RNA silencing. *Nature* 426:874-878.
6. Goldberg, K.-B., J. Kiernan, and R. J. Shepherd. 1991. A disease syndrome associated with expression of gene VI of caulimoviruses may be a nonhost reaction. *Mol. Plant-Microbe Interact.* 4:182-189
7. Chu, M., Desvoyes, B., Turina, M., Noad, R. & Scholthof, H. B. (2000) *Virology* 266, 79-87.
8. Scholthof, H. B., Scholthof, K.-B. G., Kikkert, M. & Jackson, A. O. (1995) *Virology* 213, 425-438.
9. Scholthof, H. B., Scholthof, K.-B. G. & Jackson, A. O. (1995) *Plant Cell* 7, 1157-1172.
10. Turina, M., Omarov, R., Murphy, J. F., Bazaldua-Hernandez, C., Desvoyes, B. & Scholthof, H. B. (2003) *Molec. Plant Pathol.* 4, 67-72
11. Qiu, W. P., Park, J.-W. & Scholthof, H. B. (2002) *Molec. Plant-Microbe Interact.* 15, 269-280.
12. Voinnet, O., Pinto, Y. M. & Baulcombe, D. C. (1999) *Proc. Natl. Acad. Sci. USA* 96, 14147-14152.
13. Voinnet, O., Rivas, S., Mestre, P. & Baulcombe, D. (2003) *Plant J.* 33, 949-956.
14. Scholthof, H. B., Desvoyes, B., Kuecker, J. & Whitehead, E. (1999) *Molec. Plant-Microbe Interact.* 12, 670-679.
15. Desvoyes, B., Faure-Rabasse, S., Chen, M.-H., Park, J.-W. & Scholthof, H. B. (2002) *Plant Physiol.* 129, 1521-1532.
16. McNellis, T. W., Mudgett, M. B., Li, K., Aoyama, T., Horvath, D., Chua, N. H. & Staskawicz, B. J. (1998) *Plant J.* 14, 247-257.
17. Zenklusen, D., Vinciguerra, P., Strahm, Y. & Stutz, F. (2001) *Mol. Cell. Biol.* 21, 4219-4232.
18. Qu, F. & Morris, T. J. (2002) *Molec. Plant-Microbe Interact.* 15, 193-202.

19. Omarov, R., Sparks, K., Smith, L., Zindovic, J. and Scholthof, H. B. (2006) Biological relevance of a stable biochemical interaction between the Tombusvirus-encoded P19 and short interfering RNAs, *J Virol,* 80, 3000-3008.
20. Fisher, C. L., & Pei, G K. (1997) Modification of a PCR-based site-directed mutagenesis method, *Biotechniques,* 23, 570-574.
21. Mattanovich, D., Ruker, F., Machado, A. C., Laimer, M., Regner, F., Steinkellner, H., Himmler, G., & Katinger H. (1989) *Nucleic Acids Res.* 17,6747.
22. [online], Retrieved from the Internet:<URL: http://edoc.hu-berlin.de/dissertationen/jacob-daniela-2003-07-15/HTML/chapter6.html.
23. Dr. Siddarame Gowda, personal communication.

What is claimed is:

1. A method of enhancing expression of at least one desired gene product in a plant, comprising:

transgenically introducing a Tombusvirus p19/R43W mutant gene into the genome of a plant;

expressing at least one desired gene product in said plant, wherein expression of said product is susceptible to RNAi in said plant in the absence of a RNAi suppressor; and co-expressing said transgenically introduced p19/R43W to produce an amount of P19/R43W mutant protein sufficient to suppress silencing of expression of said desired gene product, without causing lethal necrosis in said plant.

2. The method of claim 1, wherein said desired gene product is encoded by a gene that is foreign to said plant.

3. The method of claim 1, wherein said desired gene product is encoded by a gene that is endogenous to said plant.

4. The method of claim 1, wherein the plant is not a host plant for Tomato bushy stunt virus (TBSV).

5. The method of claim 1, wherein the plant is a crop plant.

6. The method of claim 5, wherein said crop plant is selected from the group consisting of sugarbeet, potato and cereals.

7. The method of claim 1, wherein said plant is *N. benthamiana* or a vegetable plant.

8. The method of claim 7, wherein said plant is a vegetable plant selected from the group consisting of tomato, pepper, cucumber, spinach, beet and lettuce.

9. The method of claim 1, wherein transgenically introducing said P19/R43W into the genome of said plant comprises transformation with an *Agrobacterium* T-DNA vector comprising an expression construct containing p19/R43W.

10. The method of claim 9, wherein said expression construct comprises pCass4N-P19/R43W.

11. The method of claim 1, wherein expressing at least one desired gene product in said plant comprises transformation with an *Agrobacterium* T-DNA vector comprising a cDNA encoding said desired product.

12. The method of claim 1, wherein said at least one desired gene product comprises a protein or peptide selected from the group consisting of reporter proteins, antibodies and fragments thereof, enzymes, growth factors, cell surface receptor molecules, seed storage proteins and fungicides.

13. The method of claim 1, wherein said at least one desired gene product comprises a gene product selected from the group consisting of gene products that regulate the synthesis of metabolites, pharmaceutical proteins and peptides, nutraceutical proteins and peptides, proteins and peptides that cannot be chemically synthesized, and proteins and peptides that require post-translational processing.

14. A transgenic plant produced by a method comprising:
transgenically introducing an expressible Tombusvirus p19/R43W mutant gene into the genome of a plant; and
expressing said transgenically introduced p19/R43W to produce an amount of P19/R43W mutant protein sufficient to suppress RNA silencing of expression of a desired gene product without causing lethal necrosis in said plant.

15. The transgenic plant of claim 14 wherein said method further comprises transgenically introducing at least one desired gene product into said plant, wherein expression of said gene product is susceptible to RNAi in said plant in the absence of a RNAi suppressor.

16. The transgenic plant of claim 14, wherein said plant co-expresses said at least one desired gene product and said P19/R43W.

17. The transgenic plant of claim 14, wherein the amount of said at least one desired gene product (per weight of plant material) produced by said transgenic plant is greater than that produced by a similar plant that lacks said transgenically introduced p19/R43W.

18. A transgenic plant comprising Tombusvirus p19/R43W mutant gene stably integrated into the genome of the plant and operably linked to a transgene encoding a desired gene product.

19. A transgenic plant comprising a gene encoding Tombusvirus p19/R43W mutant gene integrated into the genome of said plant, wherein expression of a desired protein is enhanced in said transgenic plant, and wherein expression of said desired protein is susceptible to RNAi in said plant if said p19/R43W is absent.

20. A seed from the transgenic plant of claim 18 comprising Tombusvirus p19/R43W mutant gene.

* * * * *

SEQUENCE LISTING

<160> NUMBER OF SEQ ID NOS: 4

<210> SEQ ID NO 1
<211> LENGTH: 519
<212> TYPE: DNA
<213> ORGANISM: Tomato bushy stunt virus

<400> SEQUENCE: 1

```
atggaacgag ctatacaagg aaacgacgct agggaacaag ctaacagtga acgttgggat      60
ggaggatcag gaggtaccac ttctcccttc aaacttcctg acgaaagtcc gagttggact     120
gagtggcggc tacataacga tgagacgaat tcgaatcaag ataatcccct tggtttcaag     180
gaaagctggg gtttcgggaa agttgtattt aagagatatc tcagatacga caggacggaa     240
gcttcactgc acagagtcct tggatcttgg acgggagatt cggttaacta tgcagcatct     300 cgattttcg gttcgacca gatcggatgt acctatagta ttcggtttcg aggagttagt      360
atcaccgttt ctggagggtc gcgaactctt cagcatctct gtgagatggc aattcggtct     420
aagcaagaac tgctacagct tgccccaatc gaagtggaaa gtaatgtatc aagaggatgc     480
cctgaaggta ctcaaacctt cgaaaaagaa ggcgagtaa                           519
```

<210> SEQ ID NO 2
<211> LENGTH: 172
<212> TYPE: PRT
<213> ORGANISM: Tomato bushy stunt virus

<400> SEQUENCE: 2

```
Met Glu Arg Ala Ile Gln Gly Asn Asp Ala Arg Glu Gln Ala Asn Ser
1               5                   10                  15

Glu Arg Trp Asp Gly Gly Ser Gly Thr Thr Ser Pro Phe Lys Leu
            20                  25                  30

Pro Asp Glu Ser Pro Ser Trp Thr Glu Trp Arg Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Gly Ser Arg
        115                 120                 125

Thr Leu Gln His Leu Cys Glu Met Ala Ile Arg Ser Lys Gln Glu Leu
    130                 135                 140

Leu Gln Leu Ala Pro Ile Glu Val Glu Ser Asn Val Ser Arg Gly Cys
145                 150                 155                 160
```

```
Pro Gly Gly Thr Gln Thr Phe Glu Lys Glu Gly Glu
            165                 170
```

<210> SEQ ID NO 3
<211> LENGTH: 519
<212> TYPE: DNA
<213> ORGANISM: Tomato bushy stunt virus

<400> SEQUENCE: 3

```
atggaacgag ctatacaagg aaacgacgct agggaacaag ctaacagtga acgttgggat    60
ggaggatcag gaggtaccac ttctcccttc aaacttcctg acgaaagtcc gagttggact   120
gagtggtggc tacataacga tgagacgaat tcgaatcaag ataatcccct tggtttcaag   180
gaaagctggg gtttcgggaa agttgtattt aagagatatc tcagatacga caggacggaa   240
gcttcactgc acagagtcct ggatcttggg acgggagatt cggttaacta tgcagcatct   300
cgatttttcg gtttcgacca gatcggatgt acctatagta ttcggtttcg aggagttagt   360
atcaccgttt ctggagggtc gcgaactctt cagcatctct gtgagatggc aattcggtct   420
aagcaagaac tgctacagct tgccccaatc gaagtggaaa gtaatgtatc aagaggatgc   480
cctgaaggta ctcaaacctt cgaaaaagaa ggcgagtaa                          519
```

<210> SEQ ID NO 4
<211> LENGTH: 172
<212> TYPE: PRT
<213> ORGANISM: Tomato bushy stunt virus

<400> SEQUENCE: 4

```
Met Glu Arg Ala Ile Gln Gly Asn Asp Ala Arg Glu Gln Ala Asn Ser
1               5                   10                  15

Glu Arg Trp Asp Gly Gly Ser Gly Gly Thr Thr Ser Pro Phe Lys Leu
            20                  25                  30

Pro Asp Glu Ser Pro Ser Trp Thr Glu Trp Trp Leu His Asn Asp Glu
        35                  40                  45

Thr Asn Ser Asn Gln Asp Asn Pro Leu Gly Phe Lys Glu Ser Trp Gly
    50                  55                  60

Phe Gly Lys Val Val Phe Lys Arg Tyr Leu Arg Tyr Asp Arg Thr Glu
65                  70                  75                  80

Ala Ser Leu His Arg Val Leu Gly Ser Trp Thr Gly Asp Ser Val Asn
                85                  90                  95

Tyr Ala Ala Ser Arg Phe Phe Gly Phe Asp Gln Ile Gly Cys Thr Tyr
            100                 105                 110

Ser Ile Arg Phe Arg Gly Val Ser Ile Thr Val Ser Gly Ser Arg
            115                 120                 125

Thr Leu Gln His Leu Cys Glu Met Ala Ile Arg Ser Lys Gln Glu Leu
        130                 135                 140

Leu Gln Leu Ala Pro Ile Glu Val Glu Ser Asn Val Ser Arg Gly Cys
145                 150                 155                 160

Pro Glu Gly Thr Gln Thr Phe Glu Lys Glu Gly Glu
            165                 170
```